United States Patent [19]

Smith

[11] 4,426,888
[45] Jan. 24, 1984

[54] APPARATUS FOR SAMPLING MATERIAL FROM A REMOTE LOCATION

[75] Inventor: Russell G. Smith, Cincinnati, Ohio

[73] Assignee: Xomox Corporation, Cincinnati, Ohio

[21] Appl. No.: 288,465

[22] Filed: Jul. 30, 1981

[51] Int. Cl.³ .............................................. G01N 1/10
[52] U.S. Cl. .............................. 73/863.83; 73/864.34; 376/245; 376/253
[58] Field of Search ........... 73/863.81, 863.83, 863.84, 73/864.34, 863.85, 863.71, 863.72, 863.73, 863.82, 863.86; 376/245, 253

[56] References Cited

U.S. PATENT DOCUMENTS

| | | | |
|---|---|---|---|
| 2,656,724 | 10/1953 | Cox et al. | 73/863.83 |
| 3,279,259 | 10/1966 | Haley et al. | 73/863.81 |
| 3,726,143 | 4/1973 | Enarsson | 73/863.83 |
| 3,949,614 | 4/1976 | Abonnenc | 73/863.83 |
| 4,009,618 | 3/1977 | Chatham | 73/863.83 |
| 4,147,062 | 4/1979 | Jaeger | 73/863.83 |

FOREIGN PATENT DOCUMENTS

| | | | |
|---|---|---|---|
| 1215962 | 5/1966 | Fed. Rep. of Germany | 73/863.81 |
| 63197 | 5/1968 | German Democratic Rep. | 73/863.83 |

Primary Examiner—E. R. Kazenske
Assistant Examiner—J. Chapman
Attorney, Agent, or Firm—Kinney and Schenk

[57] ABSTRACT

A system for sampling material from a remote location which selectively collects a predetermined quantity of material in a valve disposed inside a container. This measured amount of material is transferred to a movable receiving carrier while the receiving carrier is in a sealed relationship with the valve to prevent leakage of the sample material outside the receiving carrier. The movable receiving carrier is transported via an elongated tubular structure to a location remote from the container.

10 Claims, 4 Drawing Figures

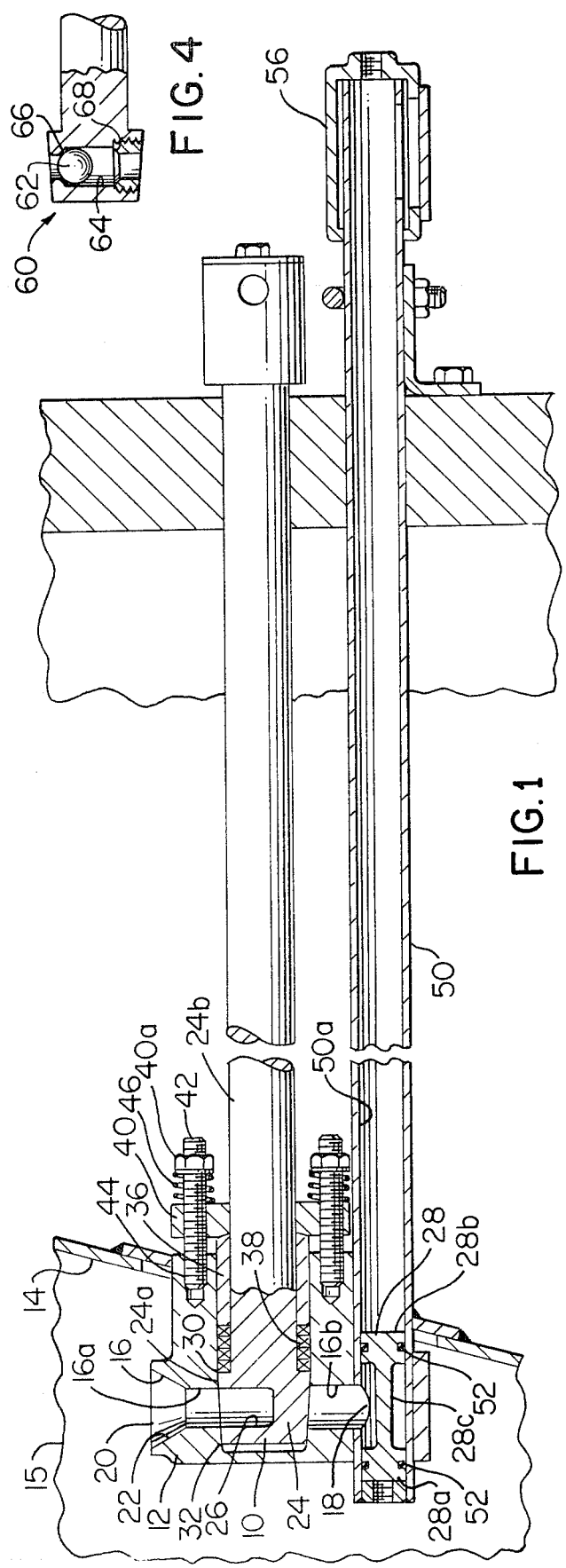
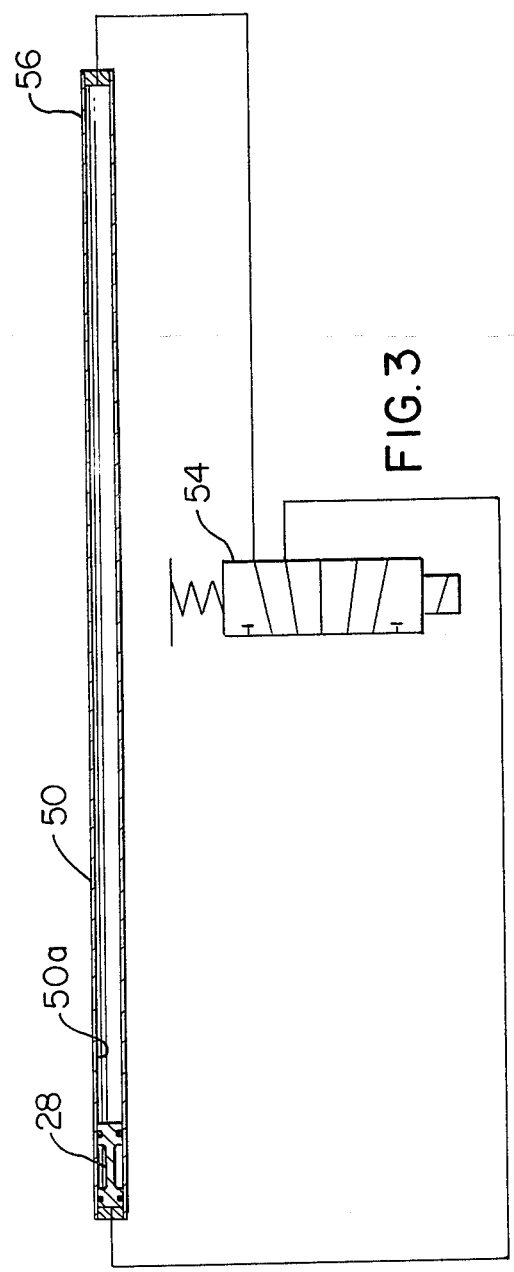
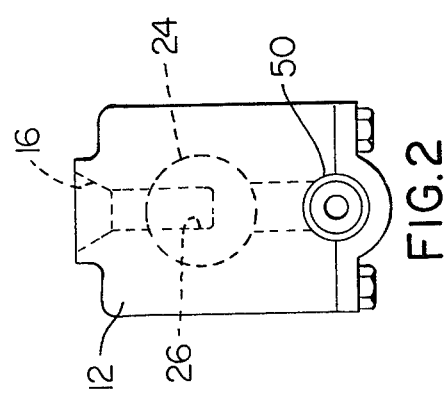

APPARATUS FOR SAMPLING MATERIAL FROM A REMOTE LOCATION

BACKGROUND

The present invention relates generally to material sampling and more particularly concerns an apparatus for sampling material from a remote location. The invention will be specifically disclosed in connection with an apparatus for collecting radioactive waste inside a hopper and transferring that radioactive waste to a discharge location outside the hopper.

It is necessary to periodically sample and test liquid and solid radioactive waste to insure that the waste material will solidify properly when a solidifying agent is added. Due to the inherent dangers associated with handling radioactive waste materials, it is highly desirable to keep such materials in containers which are shielded from human beings. When the waste material is to be tested, it is often impractical to test the material inside of its container. Accordingly, it is common practice to remove a small quantity of the waste material for sampling purposes. When sampling radioactive waste, it is obviously important to minimize any radiation leaks which might arise from removing the sample from a shielded container. This task is often complicated by the need to transport the waste material from a location inside a shielded containment vessel to a location outside the vessel.

The present invention provides an apparatus for collecting and transferring a predetermined quantity of radioactive waste material from inside a hopper to a discharge station outside the hopper with a minimum number of components traveling from inside to outside the hopper.

SUMMARY OF THE INVENTION

In accordance with the invention, a system for sampling waste material from a remote location is provided. This system includes a container for housing material to be sampled. A valve is disposed within the container and secured to a sidewall thereof so as to vertically orient a flow passage in the valve housing and to expose a top portion of that flow passage to the container contents. A rotatable valving member is disposed within the valve housing which has a recess which is in selective alignment with the flow passage. The valving member is rotatable from a first position for receiving the material to be sampled in which the recess is in alignment with the top portion of the flow passage to a second position for discharging material in which the recess is in alignment with the bottom portion of the passage. When in the second position, the valving member allows a gravity or vacuum discharge of the material to be sampled into a carrier selectively positioned beneath the rotatable valving member. The carrier receives this material discharged from the valving member and is movable from a position inside the container beneath the flow passage to a position outside the container.

The carrier is most preferably disposed within a tube structure which guides the carrier in its movement. Means are provided for applying a pressure differential to opposite ends of the carrier to propel it through the tube structure and its movements. The rotatable valving member is preferably a plug valve with a recess and most preferably a tapered plug valve which has a 360° circumferential seal between itself and the valve body. In the illustrated form, the preferred tapered plug valve is biased into a sealing fit in the valve body.

BRIEF DESCRIPTION OF THE DRAWINGS

Other objects and advantages of the invention will be apparent upon reading the following detailed description and upon reference to the drawings, in which:

FIG. 1 is a cross sectional elevational view of a preferred form of the invention which shows the carrier positioned beneath the valving member in its material receiving position.

FIG. 2 is an end view of the valve depicted in FIG. 1.

FIG. 3 is a schematic depiction of a pressurized air or vacuum system for moving the carrier from between its load and unload positions.

FIG. 4 is a fragmentary cross sectional view of a modified valving member which could be used in the embodiments of FIGS. 1 and 2.

While the invention will be disclosed in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

DETAILED DESCRIPTION OF THE PREFERRED EMBODIMENT

Referring now to the drawings and to FIG. 1 in particular, a valve 10 having a valve housing 12 is shown in secure relationship to an interior sidewall 14 of a container or hopper 15. The valve housing 12 has a vertically oriented internal flow passage 16 which extends from the top of the valve housing 12 to a discharge location 18 proximal to the bottom of the valve housing 12. Flow passage 16 commences with an opening 20 in the top portion of the valve housing 12 with an enlarged top portion 22 which converges to a cylindrically shaped flow passage 16a. A valving member 24 is interposed between the opening 20 and a bottom portion 16b of the flow passage 16 to control flow through the flow passage 16. The valving member 24 is preferably a tapered plug valve with a plug portion 24a and a stem portion 24b and is specifically illustrated as being rotatably secured in the valve body.

The plug portion 24a of the valving member 24 has a closed end recess 26 which is in selective alignment with both the top 16a and bottom 16b portions of the flow passage 16 at various times. In the illustration of FIG. 1, this recess 26 is shown in a first position in which it is in alignment with the top portion 16a of the flow passage 16. As the valving member 24 is rotated about its axis, communication with the top portion 16a of the flow passage 16 is terminated; and with 180° rotation of the valving member 24, the recess 26 is in alignment with the bottom portion 16b of the flow passage 16. As should be apparent, this recess 26 receives material dropping through the hopper 15 through the opening 20 when the valving member 24 is in the first position illustrated in FIG. 1, the material being gravity or vacuum fed into the recess through the opening 20 and top portion 16a of the flow passage 16. When the valving member 24 is rotated, communication between the top portion 16a of the flow passage 16 is terminated as the recess 26 moves out of alignment with the top portion 16a of the flow passage 16. When the valving member 24 has been rotated 180° from the illustrated position of FIG. 1, the recess 26 is then aligned with the bottom portion 16b of the flow passage 16 and material received in the recess 26 when it was in the first position is discharged under gravity or vacuum bias into a carrier 28.

The use of a tapered plug valve as the valving member 24 has been found to be most advantageous. This is because a tapered plug valve is circumferentially sealed about the recess 26 without dead space areas into which material could flow when the valving member is rotated. A non-tapered plug valve could also be used if accurately machined. However, a tapered plug valve provides a circumferential seal between the plug and the valve body about the recess without the critical fit which would be required with a non-tapered plug valve. The taper provides for an adjustable fit when fitted into a matching tapered bore in the valve body. In the illustration of FIG. 1, the taper is from left to right of the plug portion with the diameter at location 30 being greater than that at location 32. Both tapered and untapered plug valves provide 360° circumferential seals between the valve body and the valving member about the recess.

The plug portion 24a of the valving member 24 is joined by a stem portion 24b which extends outwardly of the valve body and the hopper to a remote location. At this remote location, the stem portion may be turned, either manually or by an automated actuator, and the resulting torque will be transmitted by the stem portion 24b to rotate the flow portion 24a. The valving member 24 is retained in the valve body 12 by a gland 36 which circumscribes the stem portion 24b of the valving member 24 and applies a compressive force against the tapered plug portion 24a of the valve member 24 through packing rings 38 intimately circumscribing the stem portion 24b proximal to the interface with the plug portion 24a. The gland 36 has outwardly extending studs 40 through which threaded bolts 42 extend for insertion into medially threaded and aligned openings 44 in the valve body. These bolts 42 serve to secure both the gland 36 and the valving member 24 to the valve housing 12. Compressive springs 46 are coiled about the bolts 42 and interpose between the studs 40 and nuts 40a threadably received on the outer periphery of the bolts 42 to urge the gland 36 toward the body and thus urge the tapered plug portion 24a of the valving member 24 into sealing relationship with the valve housing 12.

As mentioned above, positioned beneath the lower end of the flow passage 16b is a carrier 28. The carrier 28 has two end portions 28a and 28b of cylindrical shape with a first diametral dimension joined by an intermediate portion 28c of lesser diametral dimension which has a common central axis with the adjoining end portions 28a and 28b. The smaller diametral dimension of the intermediate portion 28c of the carrier is positioned directly beneath the flow passage 16b for reception of material from the valving member 24. Whenever so positioned, thhis intermediate or middle portion 28c of the carrier 28 receives material discharged through the flow passage 16 when the valving member 24 is rotated.

The carrier 28 is disposed in a tube structure 50 which leads to a remote location wherein it is desired to discharge the material to be sampled. Seals 52 circumscribe the enlarged end portions 28a and 28b of the carrier 28 and engage the inner periphery 50a of the tube structure 50. The carrier 28 is pneumatically propelled from a load position, which is illustrated in FIG. 1, to a discharge end 56 by the impetus of a pressure differential which is created upon opposite sides of the carrier 28.

FIG. 3 shows a schematic representation of one arrangement to pneumatically propel the carrier 28 in which a solenoid 54 is used to selectively apply air or vacuum to opposite sides of the tube structure 50. In the depiction of FIG. 3, a greater pressure has been applied to the right hand side of the tube structure 50 than to the left hand side, and the resulting pressure differential has forced the carrier 28 to the left hand side of the tube structure 50. When the cylindroid is activated, the pressure differential is reversed and the pressure on the left hand side of the carrier will exceed the pressure on the right by an amount sufficient to propel the carrier to the discharge station 56 where it will discharge material to be sampled.

FIG. 4 shows a modified valving member 60 which could be used in lieu of valving member 24 illustrated in FIG. 1. The valving member 60 is like the valving member 24 in that it has a tapered plug valve configuration. Unlike valving member 24, the valving member 60 has a spherical cleansing ball member 62 which is slidably fitted within a cylindrically shaped recess 64 extending partially through the valving member. The cleansing ball 62 has a diameter which is slightly less than that of recess 64. The cleansing ball 62 is movable within the recess between two seats 66 and 68. The seat 66 is positioned in the closed end of the recess 64 while the seat 68 is removably positioned at the open end of the recess 64. The cleansing ball 62 is positioned within the recess 64 when the seat 68 is removed from valving member 60. After the cleansing ball 62 is disposed within the recess 64, the seat 68 is threadably secured in the open end of the recess 64 permitting removal of the cleansing ball 62.

When the valving member 60 is rotated to orient the open end of the recess 64 vertically above the closed end, the cleansing ball 62 drops under gravity bias to a seated position against seat 66. In this position, the recess 64 is aligned and in communication with the top portion 16a of flow passage 16 for receipt of material traveling through the flow passage 16. Material may then fill the recess in the space above the cleansing ball 62.

When rotated 180°, the recess 64 of the valving member 60 is aligned with the bottom portion 16b of the flow passage 16 and material received in the recess 64 when it was in the earlier described position is discharged in the gravity (or vacuum) bias into the carrier 28.

Further, the gravity bias inserted on the cleansing ball 62 forces it from its seated position against seat 66 and toward seat 68. This movement of the ball 62 has a wiping effect that exerts a positive force against any accumulated material sticking to the sidewalls of recess 64. The use of a cleansing ball in this manner is highly useful with certain fine particulate material and insures that the entire measured quantity of material is discharged. The use of a cleansing ball in this manner also helps minimize cross batch contamination when different material batches pass through the flow passage 16.

Thus it has been apparent that there has been provided, in accordance with the invention, an apparatus that fully satisfies the objects, aims and advantages set forth above. While the invention has been described in conjunction with a specific embodiment thereof, it is evident that many alterations, modifications and variations will be apparent to those skilled in the art in light of the foregoing description. Accordingly, it is intended to embrace all such alternatives, modifications and variations as fall within the spirit and broad scope of the appended claims.

What is claimed is:

1. A system for sampling material from a remote location, comprising:
   (a) a container for housing material to be sampled;
   (b) a valve, said valve having a housing disposed inside of the container and having a vertically oriented flow passage with an open top portion exposed to the container contents;
   (c) a movable valving member disposed within said valve housing, said valving member having a recess which is in selective alignment with said flow passage, said valving member being movable from a first position for receiving the material to be sampled in which the recess is in alignment with the top portion of the flow passage to a second position for discharging the material to be sampled in which said recess is in alignment with the bottom portion of the flow passage; and
   (d) a carrier selectively positioned beneath the movable valving member for receiving material discharged from a valving member, said carrier being movable from a position inside the container beneath said flow passage to a position outside said container.

2. A sampling system as recited in claim 1 wherein said valve housing is secured to the sidewall of the container.

3. A sampling system as recited in claim 1 wherein said movable valving member has a 360° circumferential seal about said recess between said valve housing and said valving member.

4. A sampling system as recited in claim 3 wherein said valving member is a plug valve.

5. A valving member as recited in claim 4 wherein said plug valve is tapered.

6. A sampling system as recited in claim 1 wherein said carrier is movably disposed within a tube.

7. A sampling system as recited in claim 6 wherein said carrier is pneumatically movable within said tube.

8. A sampling system as recited in claim 5 wherein said tapered plug valve is biased into a sealing fit with said valve body.

9. A sampling system as recited in claim 6 wherein said carrier has a centrally disposed portion for receiving the material to be sampled with seals between the carrier and the tube on each side of the material receiving portion.

10. A system for sampling material from a remote location, comprising:
   a container for material to be sampled;
   a valve disposed within said container, said valve having a vertically oriented flow passage with an open top portion exposed to the container contents;
   valving means for selectively transferring a quantity of material from the top portion of said vertically oriented flow passage to a bottom portion thereof; and
   a carrier selectively positioned beneath said valve means for receiving material transferred by said valving means and transporting said received material to a remote location, said carrier being movable within an elongated tubular structure from a position inside the container beneath said valve means to a position remote from said container.

* * * * *